(12) United States Patent
Walker

(10) Patent No.: US 6,475,204 B1
(45) Date of Patent: Nov. 5, 2002

(54) DIAPER CONSTRUCTION

(76) Inventor: Doris A. Walker, 7211 Carew St., Houston, TX (US) 77074

( * ) Notice: Subject to any disclaimer, the term of this patent is extended or adjusted under 35 U.S.C. 154(b) by 0 days.

(21) Appl. No.: 09/546,301

(22) Filed: Apr. 10, 2000

(51) Int. Cl.[7] .................................................. A61F 13/15
(52) U.S. Cl. ................................................... 604/385.06
(58) Field of Search ........................ 604/385.06, 385.19

(56) References Cited

U.S. PATENT DOCUMENTS

| | | | |
|---|---|---|---|
| 4,417,894 A | 11/1983 | Norris | 604/385 |
| 4,738,678 A | 4/1988 | Paulis | 604/385 |
| 4,743,240 A | 5/1988 | Powell | 604/385 |
| 4,790,840 A | 12/1988 | Cortina | 604/385.1 |
| 4,808,175 A | 2/1989 | Hansen | 604/385.1 |
| 4,931,052 A | 6/1990 | Feldman | 604/385.1 |
| 5,241,710 A * | 9/1993 | Lockhart | 2/406 |
| D366,315 S | 1/1996 | Oranday | D24/126 |
| 5,569,230 A * | 10/1996 | Fisher et al. | 604/385.1 |
| 5,582,605 A | 12/1996 | Lepie | 604/385.1 |
| 6,004,307 A | 12/1999 | Colon et al. | 604/385.1 |

* cited by examiner

Primary Examiner—Dennis Ruhl
Assistant Examiner—C. Lynne Anderson
(74) Attorney, Agent, or Firm—Joseph N. Breaux

(57) ABSTRACT

A diaper construction wherein one or more baby wipes is included in the diaper so that the child care giver always has a baby wipe to change the diaper. To prevent removal of the baby wipes by the baby, the baby wipe is contained within a cavity of a sealed pocket member provided within the diaper that is accessible only by tearing an access opening through an outer layer of the diaper and then rupturing a wall of the pocket member to gain access to the baby wipe.

1 Claim, 1 Drawing Sheet

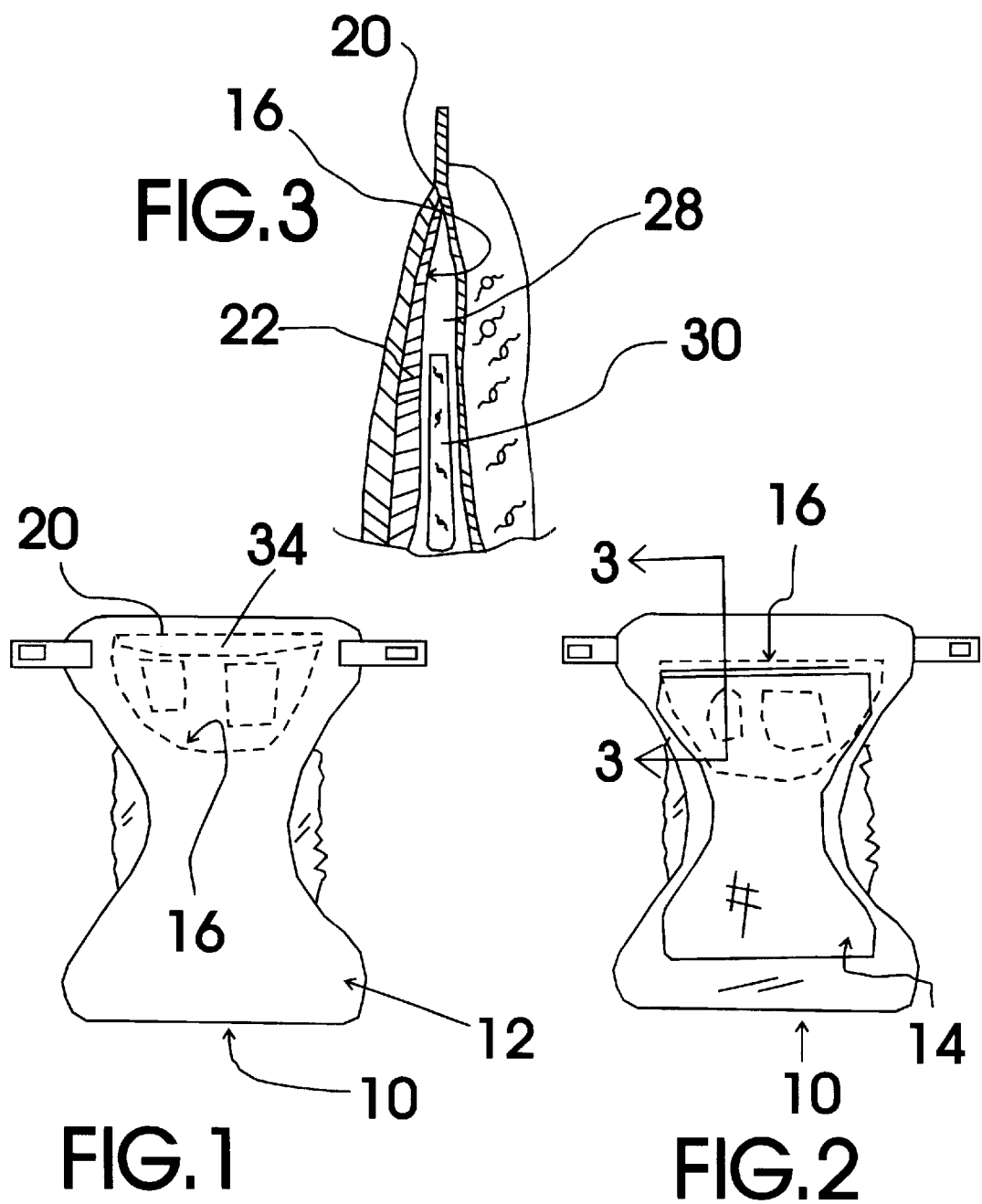

DIAPER CONSTRUCTION

TECHNICAL FIELD

The present invention relates to diaper constructions and more particularly to a diaper construction that includes a waterproof outer diaper layer, an inner absorbent diaper layer and a moisture proof pocket member adhesively secured between the waterproof outer diaper layer and the inner absorbent diaper layer; the waterproof outer diaper layer having a line of perforations provided therethrough adjacent a wall of the moisture proof pocket member; the moisture proof pocket having cavity containing a moistened baby wipe provided therein for cleaning a baby prior to putting on a new diaper; the wail of the moisture proof pocket member being accessed by tearing an access opening through waterproof outer diaper layer along the line of perforations; the cavity being accessed by rupturing the wall of the moisture proof pocket member.

BACKGROUND ART

Babies often need a diaper change in locations and at times where the usual diaper changing tools and the like are not readily available. Because each diaper change typically always requires a cleansing of the baby before the new diaper is out on, it would be a benefit to have a diaper construction wherein one or more baby wipes is included in the diaper so that the child care giver always has baby wipes to change the diaper. Because it would not be beneficial to have the child remove the bay wipe prior to use, it would be a benefit to have a diaper construction wherein the baby wipe is contained within a cavity of a sealed pocket member provided within the diaper that is accessible only by tearing an access opening through an outer layer of the diaper and then rupturing a wall of the pocket member to gain access to the baby wipe.

GENERAL SUMMARY DISCUSSION OF INVENTION

It is thus an object of the invention to provide a diaper construction that includes a waterproof outer diaper layer, an inner absorbers diaper layer and a moisture proof pocket member adhesively secured between the waterproof outer diaper layer and the inner absorbent diaper layer; the waterproof outer diaper layer having a line of perforations provided therethrough adjacent a wall of the moisture proof pocket member; the moisture proof pocket having cavity containing a moistened baby wipe provided therein for cleaning a baby prior to putting on a new diaper; the wall of the moisture proof pocket member being accessed by tearing an access opening through waterproof outer diaper layer along the line of perforations; the cavity being accessed by rupturing the wall of the moisture proof pocket member.

Accordingly, a diaper construction is provided. The diaper construction includes a waterproof outer diaper layer, an inner absorbent diaper layer and a moisture proof pocket member adhesively secured between the waterproof outer diaper layer and the inner absorbent diaper layer; the waterproof outer diaper layer having a line of perforations provided therethrough adjacent a wall of the moisture proof pocket member; the moisture proof pocket having cavity containing a moistened baby wipe provided therein for cleaning a baby prior to putting on a new diaper; the wall of the moisture proof pocket member being accessed by tearing an access opening through waterproof outer diaper layer along the line of perforations; the cavity being accessed by rupturing the wall of the moisture proof pocket member.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 1 is an exterior plan view of an exemplary embodiment of the diaper construction of the present invention showing a waterproof outer diaper layer through which a cavity of a moisture proof pocket member positioned between the outer diaper layer and the inner absorbent diaper layer is accessed via a line of perforations provided along an upper edge thereof; the moisture proof pocket having a moistened baby wipe provided therein for cleaning a baby prior to putting on a new diaper; the cavity being accessed by rupturing a wall of the moisture proof pocket member.

FIG. 2 is an interior plan view of an exemplary embodiment of the diaper construction of the present invention.

FIG. 3 is a cross sectional view along the line 3—3 of FIG. 2 showing the baby wipe positioned within the cavity of the moisture proof pocket member and the perforated line through which the moisture proof pocket member is accessed and the wall of the pocket member ruptured when accessing the cavity.

EXEMPLARY MODE FOR CARRYING OUT THE INVENTION

FIGS. 1–3 show various aspects of an exemplary embodiment of the diaper construction of the present invention generally designated 10. Diaper construction 10 includes a waterproof outer diaper layer, generally designated 12; an inner absorbent diaper layer, generally designated 14; and a moisture proof pocket member, generally designated 16 (shown in dashed lines in FIGS. 1 and 2), adhesively secured between waterproof outer diaper layer 12 and inner absorbent diaper layer 16.

Waterproof outer diaper layer 12 has a line 20 of perforations provided therethrough adjacent a wall 22 of moisture proof pocket member 16. Moisture proof pocket 16 has cavity 28 containing a moistened baby wipe 30 provided therein for cleaning a baby prior to putting on a new diaper 10. Wall 22 of moisture proof pocket member 16 is accessed by tearing an access opening 34 through waterproof outer diaper layer 12 along line 20 of perforations. Cavity 28 is accessed for removing wipe 30 by rupturing wall 22 of moisture proof pocket member 16 with the fingers of the hands or other suitable method.

It can be seen from the preceding description that a diaper construction has been provided.

It is noted that the embodiment of the diaper construction described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A diaper construction comprising:

a waterproof outer diaper layer;

an inner absorbent diaper layer; and a moisture proof pocket member adhesively secured between said waterproof outer diaper layer and said inner absorbent diaper layer;

said waterproof outer diaper layer having a line of perforations provided therethrough adjacent a wall of said moisture proof pocket member;

said moisture proof pocket having cavity containing a moistened baby wipe provided therein for cleaning a baby prior to putting on a new diaper;

said wall of said moisture proof pocket member being accessed by tearing an access opening through waterproof outer diaper layer along said line of perforations;

said cavity being accessed by rupturing said wall of said moisture proof pocket member.

* * * * *